Figure 1:
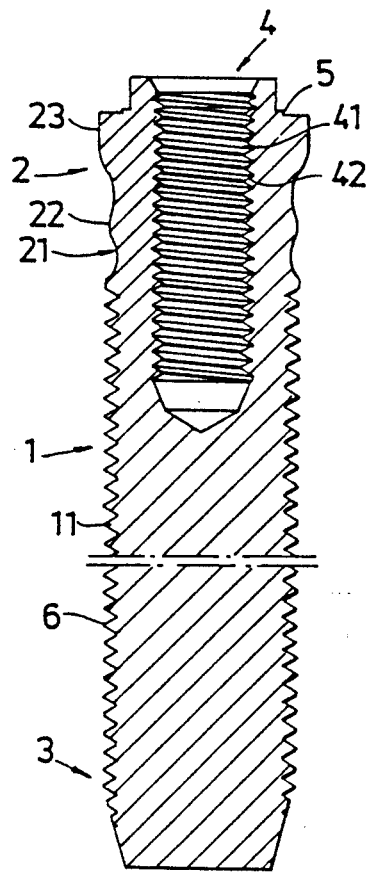

United States Patent [19]

Branemark

[11] Patent Number: 4,988,299
[45] Date of Patent: Jan. 29, 1991

[54] IMPLANT FIXTURE FOR TOOTH PROSTHESIS

[75] Inventor: Per-Ingvar Branemark, Mölndal, Sweden

[73] Assignee: The Institute for Applied Biotechnology, Sweden

[21] Appl. No.: 354,502

[22] Filed: May 19, 1989

[30] Foreign Application Priority Data

May 20, 1988 [SE] Sweden .............................. 8801886

[51] Int. Cl.⁵ .............................................. A61C 8/00
[52] U.S. Cl. ..................................................... 433/174
[58] Field of Search .............................. 433/174, 173

[56] References Cited

U.S. PATENT DOCUMENTS

| | | | |
|---|---|---|---|
| 4,466,796 | 8/1984 | Sandhaus | 433/173 |
| 4,468,200 | 8/1984 | Munch | 433/174 |
| 4,668,191 | 5/1987 | Plischka | 433/174 |
| 4,826,434 | 5/1989 | Krueger | 433/174 |

FOREIGN PATENT DOCUMENTS

| | | |
|---|---|---|
| A292209 | 4/1983 | European Pat. Off. . |
| A2111134 | 10/1983 | European Pat. Off. . |
| A2263809 | 9/1987 | European Pat. Off. . |
| 8523007 | 8/1985 | Fed. Rep. of Germany . |

Primary Examiner—Cary E. Stone
Attorney, Agent, or Firm—Ostrolenk, Faber, Gerb & Soffen

[57] ABSTRACT

A fixture intended for implanting and anchoring in bone tissue, particularly in bone tissue of the jaw, to support a prosthesis such as the crown of a tooth. The fixture has at least a surface layer of material compatible with the tissue, such as titanium. The fixture comprises a lower shaft portion with external threading and an upper, smooth, neck portion. The lower portion is arranged to be screwed into a hole drilled in the bone tissue. The diameter of the hole is substantially in agreement with the core diameter of the shaft portion. The diameter of the neck portion lies within the interval between the outer diameter of the thread on the shaft portion and the core diameter of the shaft portion. The neck portion has an axial length exceeding the settlement in bone level which normally occurs upon use of the fixture.

10 Claims, 1 Drawing Sheet

IMPLANT FIXTURE FOR TOOTH PROSTHESIS

The invention relates to a fixture intended for implanting and anchoring in bone tissue, such as bone tissue of the jaw, to support a prosthesis such as the crown of a tooth or the like, said fixture having at least a surface layer of material compatible with the tissue in a region intended to adjoin surrounding tissue, the fixture comprising a lower shaft portion with external threading and an upper, smooth, neck portion, the screw being arranged to be screwed into a hole drilled in the bone tissue, the diameter of the hole being substantially in agreement with the core diameter of the shaft portion A number of factors must be taken into consideration when implanting fixtures in the form of screws, for instance, in bone tissue, e.g. the jaw bone, to provide attachment for a superstructure, e.g. a dental prosthesis or the like.

A primary factor is of course that integration of the fixture shall occur favourably with minimum risk of infection and mechanical damage in the implantation region. Installation of the fixture must be simple and quick as well as permitting rapid integration with the surrounding tissue. The fixture and joint should of course be such that the risk of disturbance during the integration period is minimized.

A previous technique comprised the use of a fixture consisting of a cylindrical, threaded shaft with a cylindrical head, the height of the head being a fraction of the shaft diameter, and its diameter being somewhat greater than the shaft diameter, and a short, gently rounded transition portion being arranged between shaft and head. The head may have a central axial drill-hole and may be provided at its free end with formations to facilitate fitting a superstructure, e.g. the crown of a tooth or a crown base or the like.

In this connection it has been found beneficial when installing fixtures in the jaw, to apply the fixture so that the upper surface of its head lies substantially at the boundary surface between jaw bone and gum.

A hole is drilled into the jaw bone, using a drill with a diameter corresponding to the core diameter of the shaft. The drill may be applied on the fixture or the fixture itself may form the drill, for instance at the lower end of its shaft.

The threaded shaft of the fixture may suitably be arranged to cut the thread in the jaw bone for the shaft threading.

However, it has been found that upon installation of the known fixture described above, a certain bone retraction occurs.

An object of the invention is therefore to provide a fixture which, while retaining the advantageous properties described, reduces this particular drawback and provides a certain compression of the bone tissue in the immediate vicinity of the junction between the shaft and head of the screw, resulting in a dense zone in this sensitive part of the fixture-bone tissue complex.

According to the invention, this object is achieved with a screw of the type described in the introduction, which is characterised in that the diameter of the neck portion lies within the interval between the outer diameter of the thread and the core diameter of the shaft portion, the neck portion in the newly installed fixture preferably extending just above the boundary surface between bone tissue and surrounding soft tissue, and being of such a length that the shaft thread on the fixture will not be exposed after the bone level has sunk, as is normal close to the fixture after installation.

The neck portion is suitably arranged to connect continuously to a head, the diameter of which sightly exceeds the outer diameter of the shaft thread. The head may also be provided with a formation providing the foundation for a prosthesis superstructure, such as a spacer or the like, extending from the fixture through the soft tissue into the oral cavity, for instance.

The fixture or implant screw according to the invention is characterised in certain respects by its interaction with its surroundings and the invention could therefore equally well be defined as a joint. The technique described here naturally also includes the process of installing the claimed fixture in accordance with the directions revealed here.

Obviously a hole can first be drilled in the jaw bone to a diameter less than the core diameter of the shaft, and the drill member on the shaft itself can then be used to complete the pre-drilled hole when installing the fixture. Alternatively, of course, the fixture may be self-drilling and even self-threading, thus being used to produce a drill hole corresponding to the core diameter of the shaft, and to cut a thread in the wall of the hole corresponding to the outer thread of the shaft.

In this connection it should be mentioned that the integration process appears to be facilitated if the fixture is installed to surface contact with the cut in the bone tissue as quickly as possible after the wall of the hole has been cut.

A risk factor present with the known fixture is also eliminated according to the invention: during the first year a fixture of known type is in use, the level of the bone surface tends to sink slightly, thus exposing the shaft. This entailed the risk in question, i.e. accelerated settlement of the bone level caused by bacteria remaining more easily on the irregular surface presented by the exposed thread. In the present case the neck portion of the fixture is sufficiently long and is arranged, when newly installed, to extend from the region of the surface of the bone tissue down to a sufficient depth into the bone tissue, as is known per se from patent specification DE 34 21 056.

The invention will now be described by way of example, with reference to the accompanying drawing.

Figure 2:
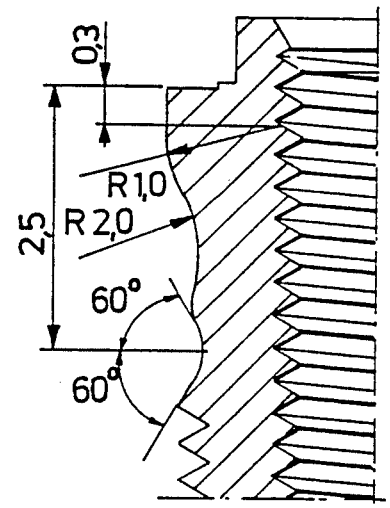
Figure 3:
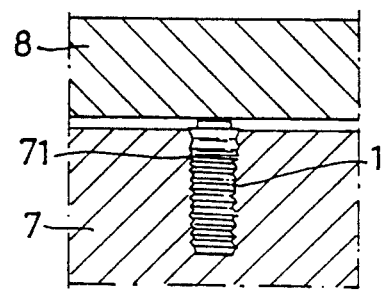

FIG. 1 shows schematically an axial section through a fixture according to the invention, FIG. 2 shows an enlarged detail of the fixture according to FIG. 1, and FIG. 3 shows schematically the fixture according to the invention when installed.

FIG. 1 shows a fixture having the general shape of a screw. The fixture comprises an externally threaded portion 6, a screw tip 3, a neck portion 2 and a head 4. The head 4 is provided with a central bore 4 with internal threading 42 onto which a superstructure such as the crown of a tooth can be screwed after the fixture 1 has integrated into the bone tissue of the jaw, for instance. The head 4 may also be provided with suitable formations 5 to support spacers for tooth crowns or the like on the fixture 1, ensuring that they do not rotate. The tip 3 of the shaft 6 may be designed in a manner not shown here, to cut a drill hole in bone tissue corresponding to the core diameter of the shaft 6, the thread 11 being arranged to cut a groove in the wall of the drilled hole.

At the upper end of the fixture head is a substantially cylindrical section 23, the diameter of which is slightly greater than the outer diameter of the shaft thread 6. In a region between the upper end of the thread 11 and the head portion 23 is a cylindrical neck portion 22 which, via a gently curving portion at 21, is connected to the upper end of the thread 11. The upper part of the cylindrical neck portion 22 is continuously connected via two radii to the head portion 23 (see FIG 2).

In a specific embodiment the thread 11 is M 3.75. The cylindrical neck portion 22 may then have a diameter of 3.4 mm, in which case the waist 21 has a diameter of 3.15 mm. The head portion 23 may then have a diameter of 4.1 mm.

FIG. 3 shows schematically bone tissue 7 is a jaw, for instance, and gum 8 located above the bore tissue. A hole is drilled in the bone tissue 71, having a diameter corresponding to the core diameter of the shaft 6. The fixture 1 is then screwed in, at the same time cutting a groove for its thread 11, to the depth shown in FIG. 3, i.e. so that the upper end of the fixture is located substantially in the boundary surface between jaw bone 7 and gum 8, whereafter the soft tissue is closed over the fixture. The fixture 1 may then be allowed to integrate into the bone tissue 7 for a sufficient length of time, after which the soft tissue is opened and the superstructure is applied on the fixture in known manner.

The invention has been described with reference to a fixture designed for carrying dental prostheses. However, it should be clear that the invention is applicable to the anchoring of any kind of prosthesis, no]only dental prostheses.

The diameter of the neck portion is suitable in the mid-region of the interval between the outer and inner diameters of the thread, the central interval being preferably centered and comprising, for instance 80%, or more preferably 60%, of the interval. The diameter of the neck portion may thus advantageously be substantially equivalent to the mean value of the inner and outer diameters of the shaft thread.

What is claimed:

1. A fixture intended for implanting and anchoring in bone tissue to support a prosthesis, the fixture having at least a surface layer of material compatible with the bone tissue, the fixture comprising a lower shaft portion with external threading and the lower shaft portion having a core diameter, the lower shaft portion being arranged to be screwed into a hole drilled in the bone tissue, wherein the diameter of the hole in the bone tissue is substantially in agreement with the core diameter of the lower shaft portion, the fixture further comprising an upper, smooth, neck portion above the lower shaft portion, the diameter of the neck portion lies within the interval between the outer diameter of the thread on the lower shaft portion and the core diameter of the shaft portion, the neck portion having an upper part away from the lower shaft portion, and a substantially cylindrical head portion at the upper part of the neck portion.

2. A fixture as claimed in claim 1, wherein the neck portion has a lower part, a waist connecting the lower part of the neck portion to the threading of the shaft portion, the waist having a diameter which is greater than the core diameter of the shaft and smaller than the diameter of the neck portion.

3. A fixture as claimed in claim 2, wherein the upper part of the neck portion is connected via a substantially continuously curved surface to the cylindrical head portion, the head portion having a diameter substantially at least equivalent to the outer diameter of the thread on the shaft.

4. A fixture as claimed in claim 2, wherein the neck portion has an axial length selected to exceed the settlement in bone level which normally occurs upon use of the fixture.

5. A fixture as claimed in claim 1, wherein the upper part of the neck portion is connected via a substantially continuously curved surface to the cylindrical head portion, the head portion having a diameter substantially at least equivalent to the outer diameter of the thread on the shaft.

6. A fixture as claimed in claim 5, wherein the neck portion has an axial length selected to exceed the settlement in bone level which normally occurs upon use of the fixture.

7. The fixture of claim 5, wherein the head portion has a diameter that is slightly greater than the outer diameter of the thread on the shaft.

8. A fixture as claimed in claim 1, wherein the neck portion (22) has an axial length selected to exceed the settlement in bone level which normally occurs upon use of the fixture.

9. A fixture as claimed in claim 1, wherein the fixture is adapted for being implanted and anchored in the bone tissue of a jaw and the prosthesis is a crown of a tooth.

10. The fixture of claim 1, wherein the material of the fixture is titanium.

* * * * *